(12) United States Patent
Butlin et al.

(10) Patent No.: US 8,647,285 B2
(45) Date of Patent: Feb. 11, 2014

(54) FLUID SAMPLE COLLECTION SYSTEM

(75) Inventors: Nathaniel G. Butlin, Pacifica, CA (US); Charles A. Martin, Santa Ana, CA (US)

(73) Assignee: Biophor Diagnostics, Inc., Redwood City, CA (US)

( * ) Notice: Subject to any disclaimer, the term of this patent is extended or adjusted under 35 U.S.C. 154(b) by 0 days.

(21) Appl. No.: 12/905,739

(22) Filed: Oct. 15, 2010

(65) Prior Publication Data

US 2011/0028863 A1 Feb. 3, 2011

Related U.S. Application Data

(63) Continuation-in-part of application No. 12/838,823, filed on Jul. 19, 2010, now abandoned.

(60) Provisional application No. 61/271,110, filed on Jul. 17, 2009, provisional application No. 61/283,284, filed on Dec. 2, 2009.

(51) Int. Cl.
*A61B 5/00* (2006.01)
*B65D 81/00* (2006.01)

(52) U.S. Cl.
USPC ........................................................ 600/573

(58) Field of Classification Search
USPC ........................................................ 600/573
See application file for complete search history.

(56) References Cited

U.S. PATENT DOCUMENTS

| | | | | |
|---|---|---|---|---|
| 3,499,327 A * | 3/1970 | Lane, Jr. | ..................... | 73/863.52 |
| 4,064,760 A * | 12/1977 | Benjamin | ................... | 73/863.52 |
| 4,852,584 A * | 8/1989 | Selby | ............................ | 600/573 |
| 5,423,792 A * | 6/1995 | Oxley | ........................... | 604/409 |
| 5,762,120 A * | 6/1998 | Smith | ........................... | 141/340 |

FOREIGN PATENT DOCUMENTS

GB 2218338 * 11/1989

OTHER PUBLICATIONS

Mountain Homebrew and Wine Supply—Funnel 10" Slant Style. Dec. 28, 2006.*
Monster Brew—8 inch Anti splash funnel.*

* cited by examiner

*Primary Examiner* — Brian Szmal
*Assistant Examiner* — H. Q. Nguyen

(57) ABSTRACT

A sample collection container adapted to be connected to, and disconnected from, a sample collection adapter and a sample collection container cap. The sample collection adapter has a downward sloping interior surface that provides a free-flowing path for samples provided by a subject to the sample collection container. The sample collection adapter may have a three-dimensional rim that is curved in two different non-parallel planes.

20 Claims, 22 Drawing Sheets

FLUID SAMPLE COLLECTION SYSTEM

CROSS-REFERENCE TO RELATED APPLICATIONS

This application is a continuation in part of U.S. application Ser. No. 12/838,823, filed Jul. 19, 2010, which claims priority of U.S. Provisional Application No. 61/271,110, filed Jul. 17, 2009. This application is also related to U.S. Provisional Application No. 61/283,284, filed Dec. 2, 2009. The aforementioned applications are herein expressly incorporated by reference in their entirety.

BACKGROUND OF THE INVENTION

1. Field of the Invention

The present invention relates to fluid sample collection. In particular, the invention relates to a system for collecting oral fluid samples.

2. Description of Related Art

Small quantities of materials for analysis are frequently required from subjects undergoing testing for a multitude of conditions, diseases, or the presence of pharmacologically relevant molecules that are either naturally produced or introduced into the body. For example, oral fluids may be required and used as the analytical matrix. One approach to oral fluid sample collection is to place an absorbent material in the oral cavity so that a quantity may be absorbed and subsequently transferred to a container along the with absorbent material.

Another common technique for sample collection is to have a subject expectorate into a container. Such containers may have an attachment to aid in sample collection and serve as a source for additional fluid to be mixed with the sample being obtained. The additional fluid may serve to wash the sample into the container and/or stabilize the sample.

For oral fluid samples that are collected without the use of absorbents or the addition of other fluid, the efficiency of sample collection is dependent upon the geometry of the collection device, and it is desirable that the device used for collection provide a free-flowing path to the sample container.

It is desirable that the receiver for the expectorated sample be large enough that any spray or splatter is contained and channeled into the collection tube. It is also desirable that the volume and weight of the sample container be minimized to reduce the cost of transportation and ease of handling. It is preferable that the sample container falls within the specifications of standard laboratory ware for sample handling. A sample collection device that can use an effectively large sample collection adapter during the collection process, which is then discarded once the sample container is sealed, is also preferred.

A subject providing an oral fluid sample may be less than comfortable with the act of spitting into a tube, and it is desirable that a collection device be easy to use and minimize discomfort on the part of the subject. In some cases the subjects discomfort can be mitigated with the use of a shielding apparatus that offers some privacy from the view of people other than the subject.

Some analytes may have an affinity for a collection swab or pad material due to the general nature of the compound and the material's physical properties. In some cases, this affinity will reduce the accuracy of subsequent sample analysis.

The volume of oral fluid that is absorbed by collection pads or swabs is highly variable due to many factors including collection time and oral fluid viscosity and constitution. Collection devices that place a saturated adsorbent pad or swab into a fixed volume admixture have reduced analysis accuracy due to the imprecision of the sample volume.

In cases where an adsorbent pad is used, there is additional processing required to separate the sample from the pad prior to analysis. This process can include vigorous mixing, vortexing, centrifugation or other more manual methods to retrieve the sample. These processing steps are inefficient and costly, making this type of collection undesirable.

Generally, automated or robotic liquid handling instruments demonstrate improved performance with samples that do not contain significant solids or semi-solids due to precise volume sampling that must be performed. Thus it is preferred that samples do not contain significant solids.

A sample container that is directly compatible with automated robotic sample handling and processing is desirable. A sample that can be placed directly into automatic processing line is preferred. It is also preferable that the collected sample container be adapted for automated handling as received from the collection, or with minor handling such as cap removal.

Thus, a need exists for an efficient system for collecting oral fluid samples without absorbents or admixtures of significant volume. There is also a need for a sample collection system that is easy to use.

BRIEF SUMMARY OF THE INVENTION

The present invention provides a sample collection adapter that couples to a sample collection container. The adapter funnels a liquid sample provided by a subject into a container. The adapter may subsequently be replaced by a cap to seal the sample in the sample collection container.

In one embodiment of the invention the sample collection adapter is a conical funnel. The conical funnel has a female thread that allows the funnel to be connected to and disconnected from a sample collection container with a male thread.

In another embodiment, the sample collection adapter is ergonomically shaped to assist in the collection of liquid samples. The rim of the proximal opening of the sample collection adapter is a three-dimensional surface with a portion that is curved in two different planes.

DETAILED DESCRIPTION OF THE INVENTION

Figure 1A:
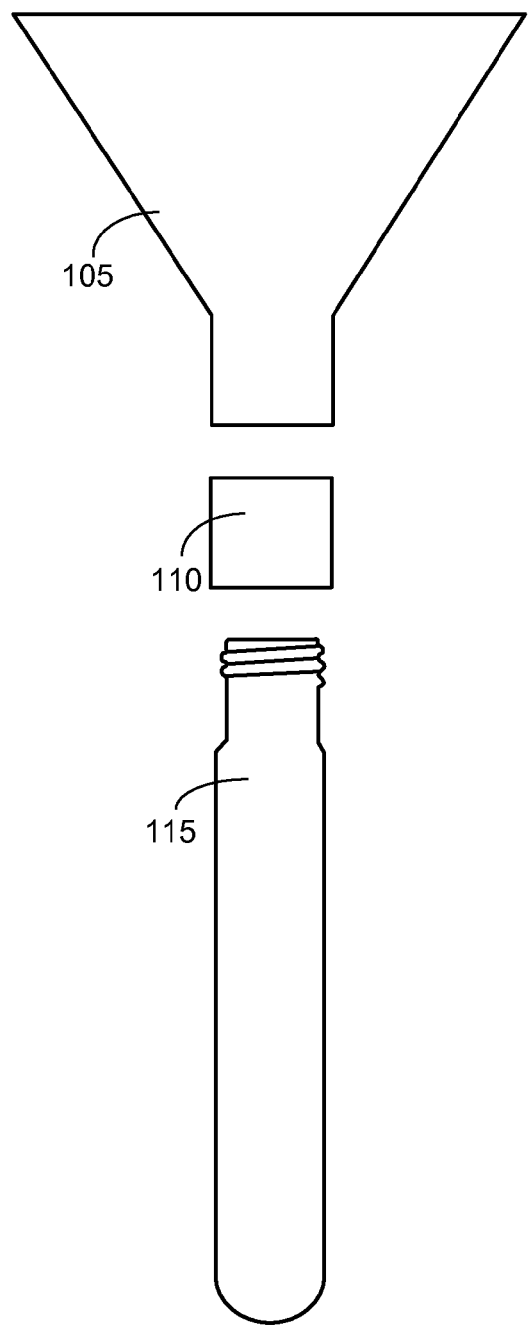
FIG. 1A shows a side view of a sample collection system in accordance with an embodiment of the present invention.
Figure 1B:
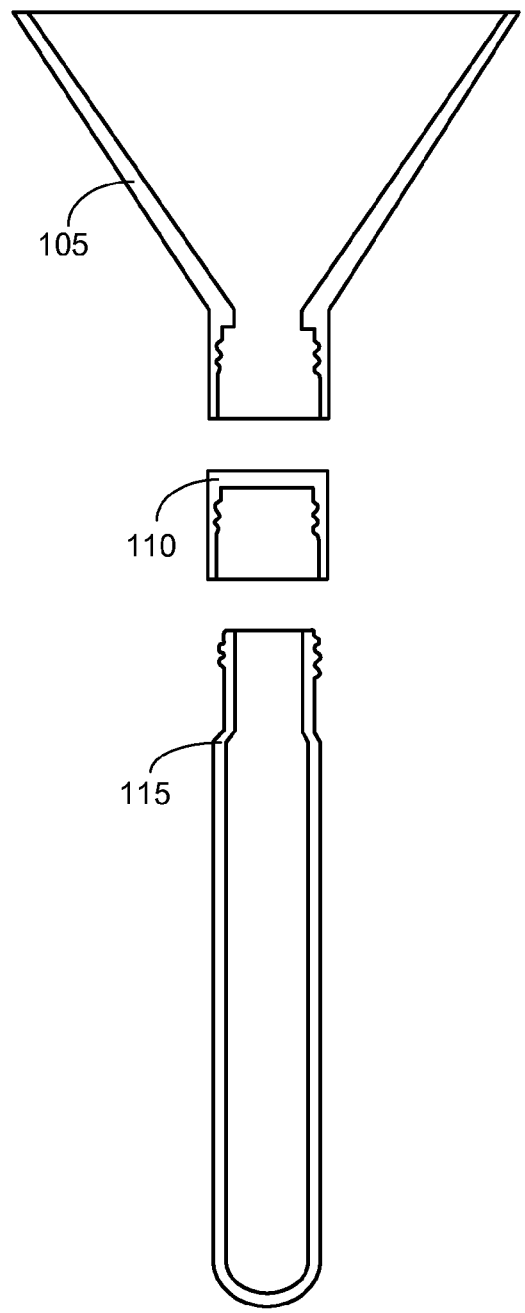
FIG. 1B shows a section view of the sample collection system of FIG. 1A.

FIG. 1A shows a side view 100 of an embodiment of a sample collection system. The sample collection system includes a conical funnel 105, a container cap 110 and a sample container 115. FIG. 1B shows a section view 101 of the sample collection system of FIG. 1A. The conical funnel 105 has a female thread that allows it to be connected to and disconnected from the sample container 115 for collection of a sample. The container cap 110 is threaded, allowing it to be connected to the sample container 115 after collection of a sample in order to provide a seal for the sample container 115.

Although the embodiment of FIG. 1A relies upon a threaded connection for the attachment of the conical funnel 105 or container cap 110 to the sample container 115, other methods of attachment may be used. For example, a snap closure may be used.

Referring to FIG. 1B, the conical funnel 105 has a sloping inner surface that provides a free-flowing path from the upper opening to the lower opening when the device is held upright in the collection orientation. The conical funnel 105 is preferably fabricated from a material that is capable of being injection molded, such as a thermoplastic polymer (e.g., polyethylene). The conical funnel 105 is also preferably opaque so that it is capable of shielding a subject's mouth from view. In an alternative embodiment, the optical transmittance of the conical funnel 105 in the visible spectrum is less than 10%.

Figure 2:
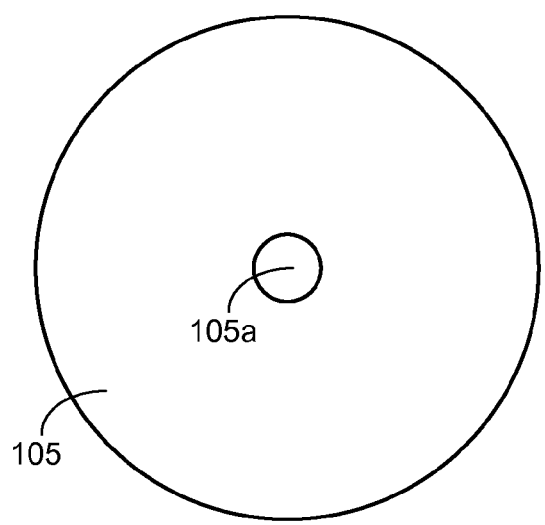
FIG. 2 shows a top view of the funnel device shown in FIG. 1A.

FIG. 2 shows a top view 200 of the conical funnel 105 shown in FIG. 1A. In one embodiment the inner diameter of the aperture 105a is equivalent to the inner diameter of the opening of the sample container 115.

Figure 3:
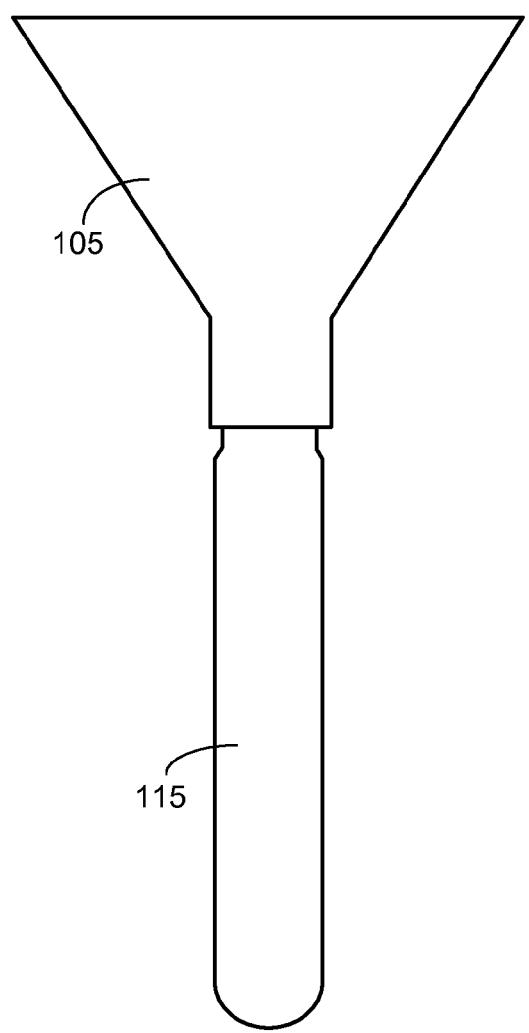
FIG. 3 shows a side view of an assembled sample collection device in accordance with an embodiment of the present invention.

FIG. 3 shows a side view 300 of an embodiment of an assembled sample collection device, with the conical funnel 105 connected to the sample container 115. The conical funnel 105 may be replaced by the container cap 110 of FIG. 1A after a sample has been collected. The conical funnel 105 and container cap 110 may provide a liquid tight seal when connected to said sample container 115.

Figure 4A:
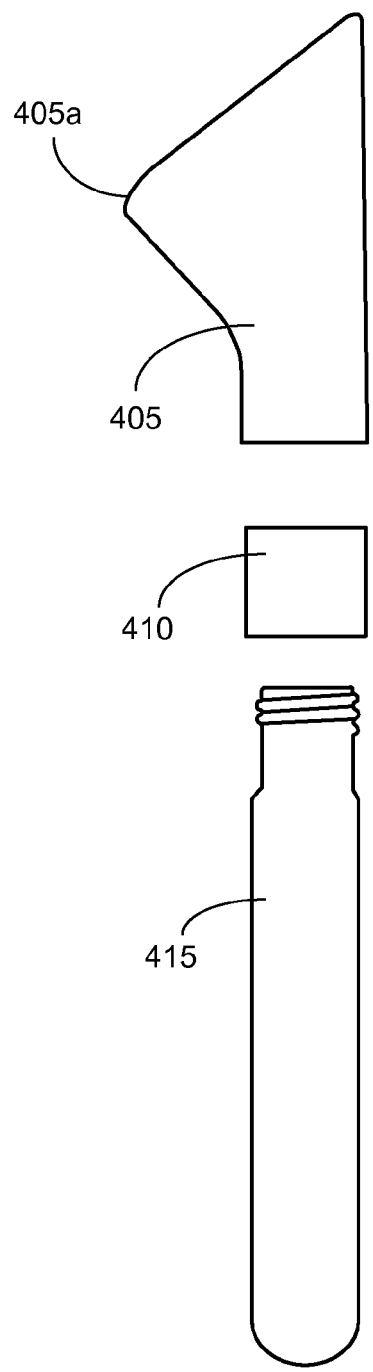
FIG. 4A shows a side view of an ergonomic sample collection system in accordance with an embodiment of the present invention.
Figure 4B:
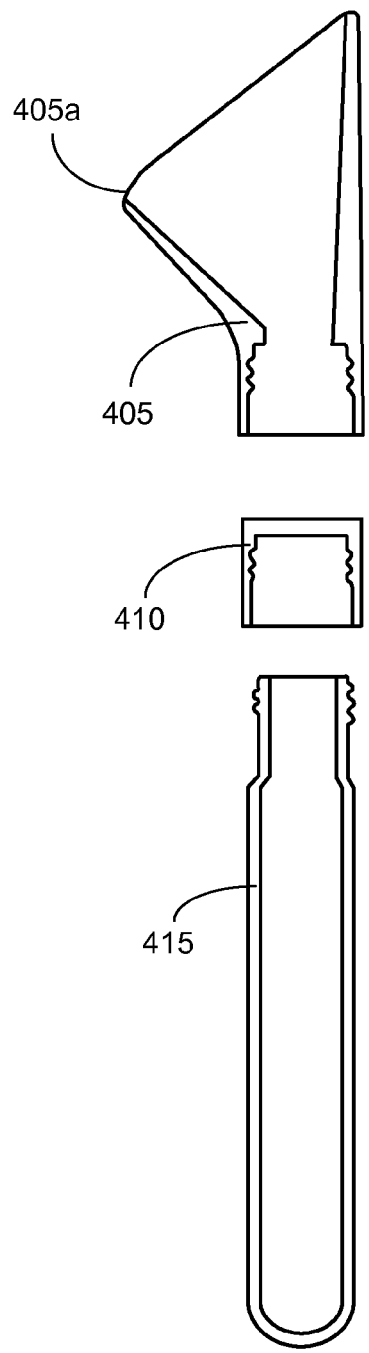
FIG. 4B shows a section view of an ergonomic sample collection system shown in FIG. 4A.

FIG. 4A shows a side view 400 of an embodiment of a sample collection system. The sample collection system includes an ergonomic funnel 405, a container cap 410 and a sample container 415. FIG. 4B shows a section view 401 of the ergonomic sample collection system shown in FIG. 4A. The rim 405a of the ergonomic funnel 405 is a three-dimensional surface that resides largely in a first plane, as can be seen in FIGS. 4A and 4B, and has a lower portion that is concave in a second non-parallel plane. The three-dimensional surface provides enhanced conformation to the mouth region of a subject providing a sample and visible shielding of the subjects mouth and specimen.

Although the embodiment of FIG. 4A relies upon a threaded connection for the attachment of the ergonomic funnel 405 or container cap 410 to the sample container 415, other methods of attachment may be used. For example, a snap closure may be used.

Figure 5A:
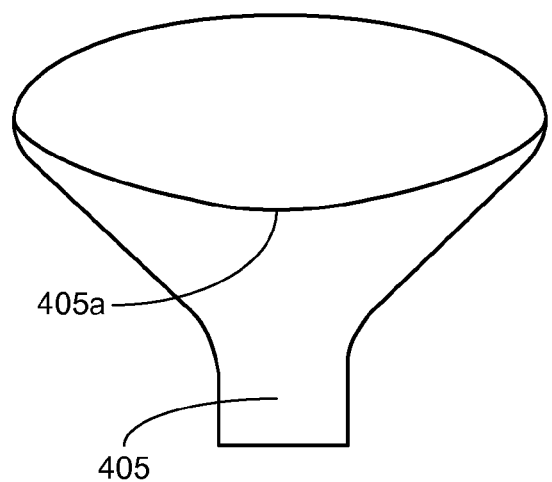
FIG. 5A shows an orthogonal side view of the ergonomic funnel device shown in FIG. 4A.
Figure 5B:
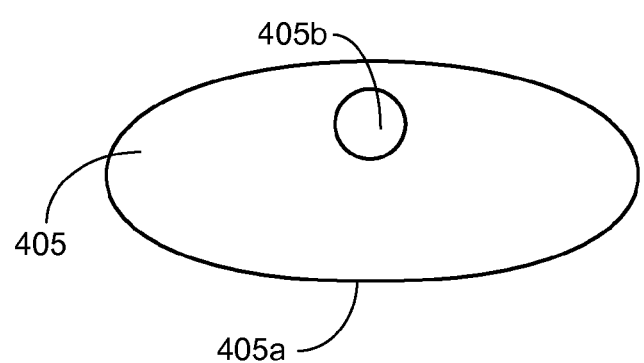
FIG. 5B shows a top view of the ergonomic funnel device shown in FIG. 5.

FIG. 5A shows an orthogonal front view 500 of the ergonomic funnel device shown in FIGS. 4A and 4B. FIG. 5B shows a top view 501 of the ergonomic funnel 405 shown in FIG. 5. The ergonomic funnel 405 has a sloping inner surface when the device is held upright in the collection orientation that provides a free-flowing path from the upper opening to the lower opening. In one embodiment the inner diameter of the aperture 405b is equivalent to the inner diameter of the opening of the sample container 115. In another embodiment the two openings do not share a common center point or diameter.

The ergonomic funnel 405 is preferably fabricated from a material that is capable of being injection molded, such as a thermoplastic polymer (e.g., polyethylene). The ergonomic funnel 405 is also preferably opaque so that it is capable of shielding a subject's mouth from view. In an alternative embodiment, the optical transmittance of the conical funnel in the visible spectrum is less than 10%.

Figure 6:
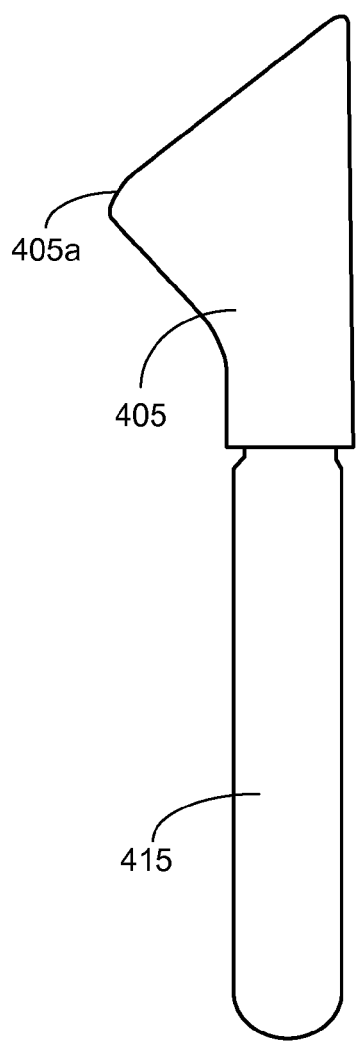
FIG. 6 shows a side view of an assembled ergonomic collection device in accordance with an embodiment of the present invention.

FIG. 6 shows a side view 600 of an embodiment of an assembled ergonomic sample collection device, with the ergonomic funnel 405 connected to the sample container 415. The ergonomic funnel 405 may be replaced by the container cap 410 of FIG. 4A after a sample has been collected. The ergonomic funnel 405 and container cap 410 may provide a liquid tight seal when connected to said sample container 415.

Figure 7A:
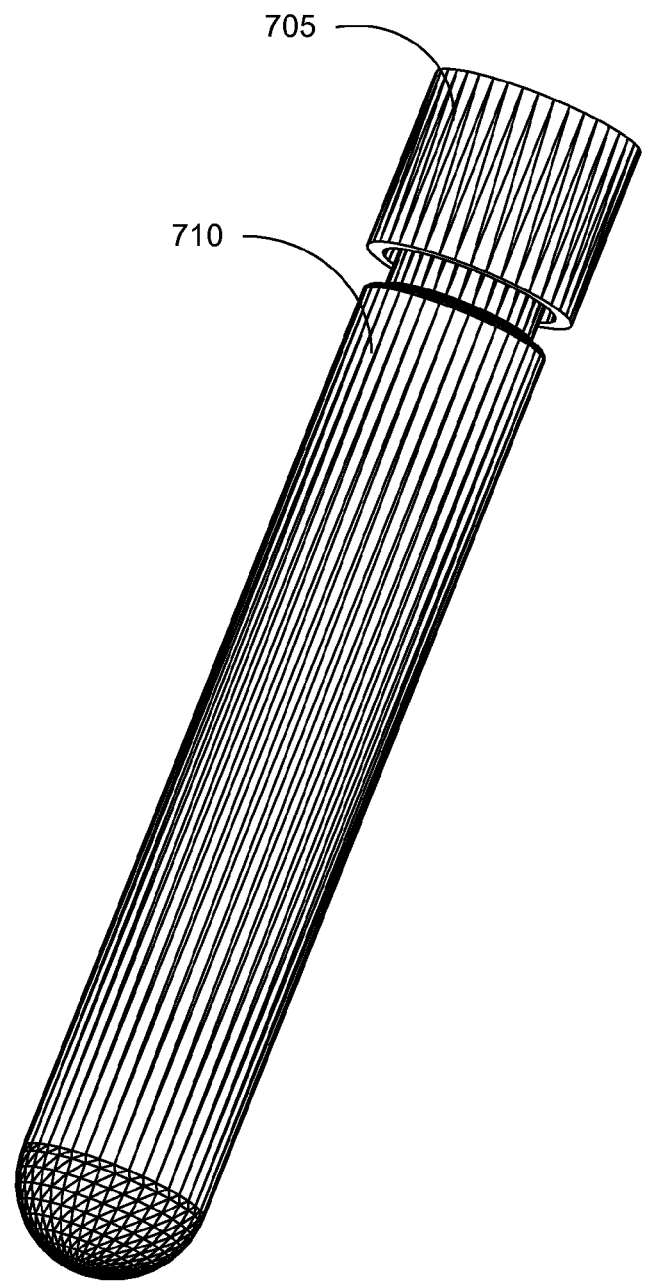
FIG. 7A shows a perspective view of a sample containment system in accordance with an embodiment of the present invention.

FIG. 7A shows a perspective view 700 of an embodiment of a sample containment system. A sample container closure 705 provides a liquid proof seal. In a preferred embodiment, the interior surfaces are sorption neutral with respect to analytes contained within the sample containment system. For purposes of this disclosure, a sorption neutral surface is a surface that does not alter the bulk concentration of a given species within the bulk of the sample.

The funnel may be made from polymeric hydrocarbons including but not limited to polyethylene terephthalate, high density polyethylene, vinyl, low density polyethylene, polypropylene, polystyrene, polytetrafluoroethylene, polyurethane, polycaprolactam, their copolymers, with or without additives for modification of physical properties including strength, flexibility, color, durability, hardness, inertness, structural stability, plasticity, and ease or cost of manufacture.

The sample container may be manufactured from any material that exhibits an effectively neutral adsorption and leaching profile relative to the sample. Specifically that the sample collection tube material has no significant adsorption, leaching, or absorption characteristics for the sample or sample analytes contained therein. A preferred embodiment of this material is borosilicate glass. A further preferred embodiment would be a sample collection tube manufactured from polytetrafluoroethylene, or an interior coating of polytetrafluoroethylene with the bulk of the tube manufactured from any structurally acceptable material including plastics. Neutral sorption material is relevant to the intended analyte or analytes of interest. For example, a specific sample container material may be suitable for analyte A but not for a second specified analyte B due to the neutral adsorption properties of the material for analyte A but not analyte B. This principle is extended to multiple analytes that share adsorption properties of analyte A and B as described above.

Additives may be used to improve the performance of the collection device. These may be combined with the sample after the sample is dispensed into the collection tube or may be present in the collection tube prior to sample collection. Additives may be visible to the eye as a fluid or solid but would preferably be of insignificant volume rendering visualization difficult for the casual observer. In one preferred embodiment the additive will have negligible impact on the sample volume. In a further preferred embodiment the additive will be coated onto the interior surface of the sample collection tube such that it would become solubulized within the sample following sample introduction.

Additives may include sample stabilizers including but not limited to analyte stabilizers, bacteriocides, fungicides, light absorbing elements, pH indicators, pH buffering agents, surfactants, solubilizing agents, active or activatable derivatizing agents, proteins and internal standards for analysis.

Figure 7B:
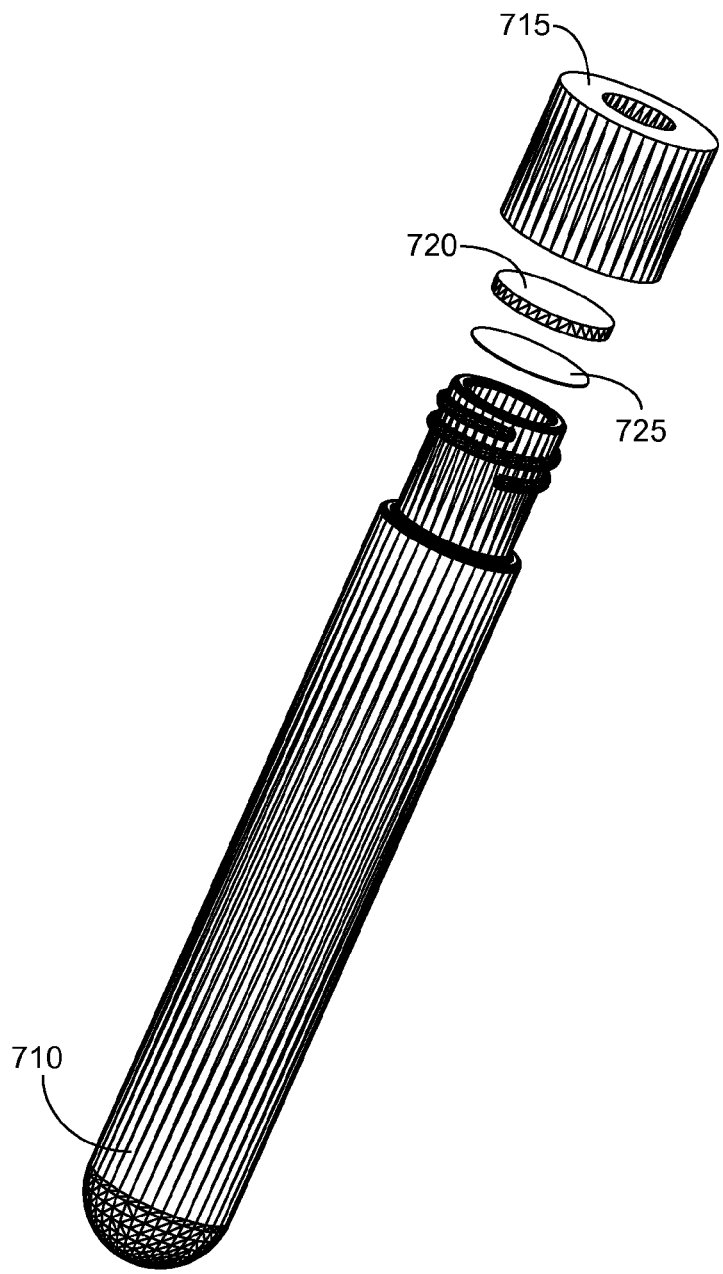
FIG. 7B shows an exploded view of the sample containment system of FIG. 7A.

FIG. 7B shows an exploded view 701 of the sample containment system of FIG. 7A. The sample container closure 705 of FIG. 7A includes a cap 715, a compression disk 720 and a closure liner 725. Although a seal may be obtained by using a cap 715 and a closure liner 725 without a compression disk 720, the combination of a closure liner 715 and a compression disk 720 provides greater flexibility in obtaining a secure seal while providing a sorption neutral surface.

The closure liner 725 may be bonded to the compression disk 720 (e.g., adhesive bonded) and the compression disk 720 may be bonded to the cap 715 (e.g., adhesive bonded). The hole in the cap 715 is optional and allows the compression disk 720 to serve as a septum through which materials may be introduced or withdrawn (e.g., by syringe).

The compression disk 720 is preferably fabricated from an elastomeric material that has a low compression set, and the liner is preferably fabricated from a material that is sorption neutral and chemically inert with respect to the sample contained within the sample container 710.

Figure 7C:
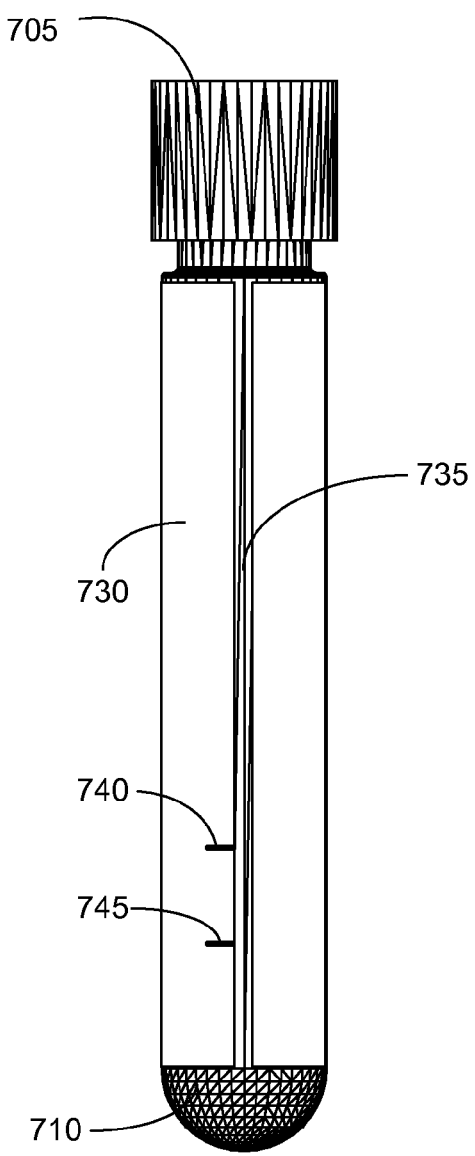
FIG. 7C shows a side view of the sample containment system of FIG. 7A with added privacy label.

FIG. 7C shows a side view 702 of the sample containment system of FIG. 7A with an added label 730. The label 730 includes a maximum fill marking 740 and a minimum fill marking 745. In one embodiment the label utilizes an adhesive for attachment to the sample container. In an alternative embodiment the label including the maximum fill marking 740 and minimum fill marking 745 are fabricated directly on the surface of sample container 710. In another embodiment the label is adhered to the sample container by friction only including a sleeve, elastomeric wrap or preprinted heatshrink polymer that is applied around the tube to form a tight fit.

In a further alternate embodiment, the label 730 creates an opaque surface on the sample container that significantly reduces visual access to the interior sample by at least 50%, except where shown for sample volume verification.

The label 730 may be fabricated from an adhesive backed printable polymer film or paper sheet. The label width may be less than the outer circumference of the sample container so that a label gap 735 is provided. The label gap 735 allows the level of the sample contents within the sample container 710 to be viewed when the sample container is fabricated from a transparent material (e.g., borosilicate glass). The label may also contain a cutout window for sample volume visualization while the label edge is the same or greater than the outer circumference of the sample container.

Figure 7D:
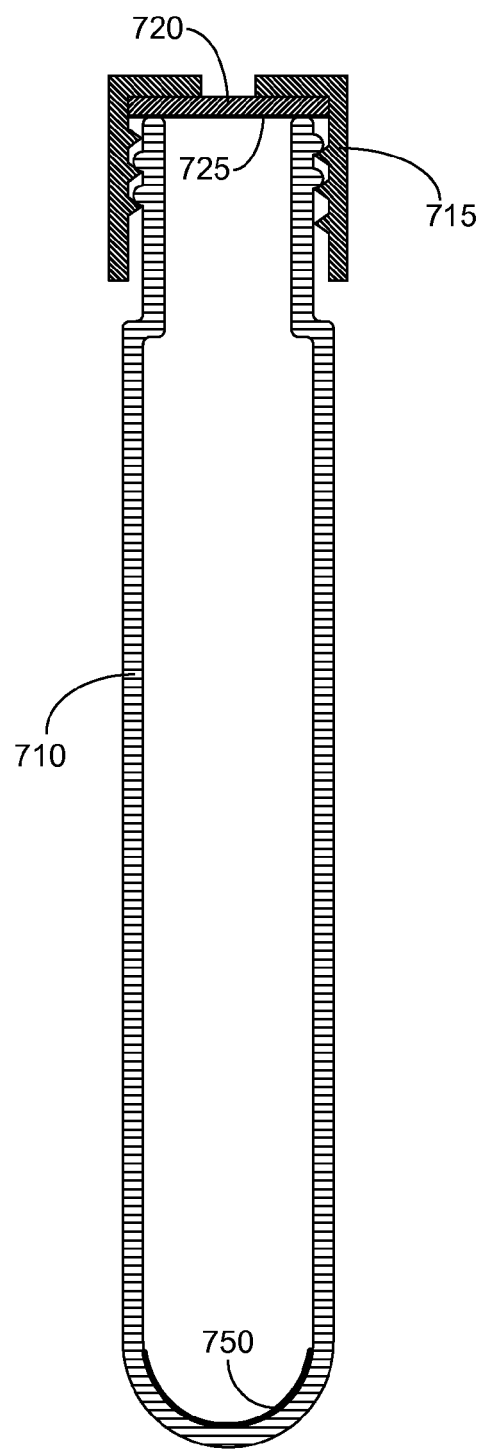
FIG. 7D shows a section view of the sample containment system of FIG. 7A.

FIG. 7D shows a section view 703 of the sample containment system of FIG. 7A. An additive coating 750 is disposed on the interior surface of the sample container 710. The coating 750 may be an antifungal or antimicrobial agent, or other material to aid in stabilizing the sample contained with the sample container 710.

Figure 7E:
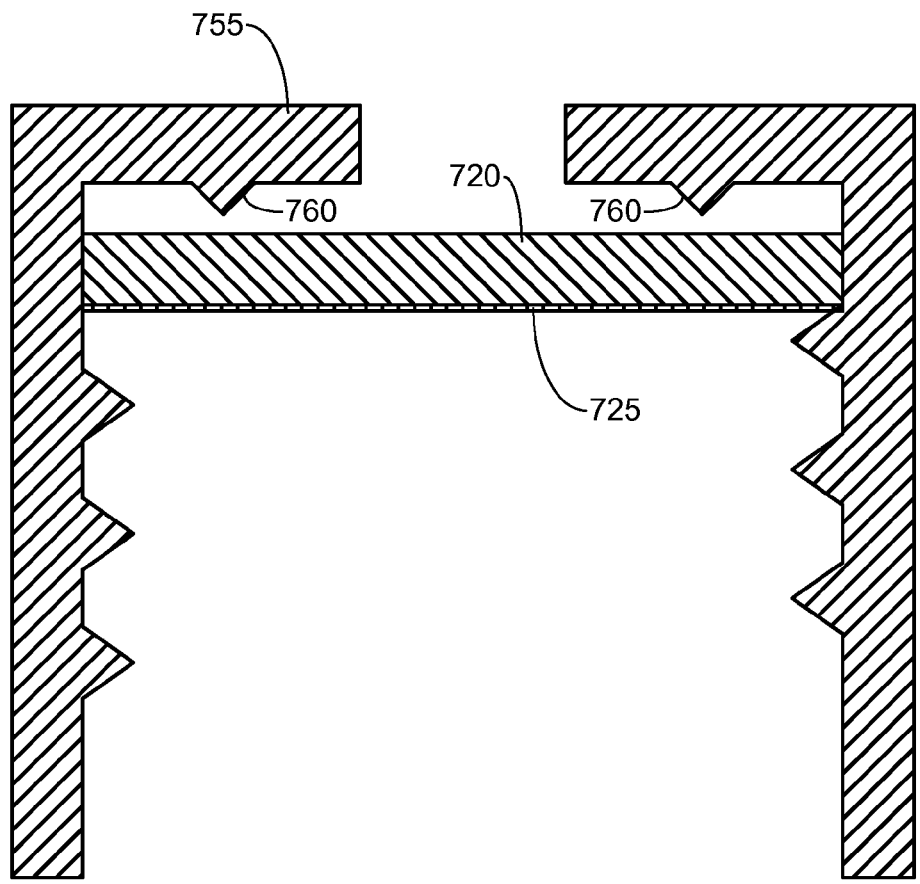
FIG. 7E shows a section view of a sample container closure in accordance with an embodiment of the present invention.

FIG. 7E shows a section view 704 of an embodiment of a sample container closure. In contrast to the cap 715 shown in FIG. 7D, clamping cap 755 of FIG. 7E has an annular protrusion 760 that reduces inward radial extrusion of the outer portion of the compression disk 720. The cross-section of the annular protrusion is triangular; however, in other embodiments the cross-section may be curved (e.g., semi-circular).

Figure 8:
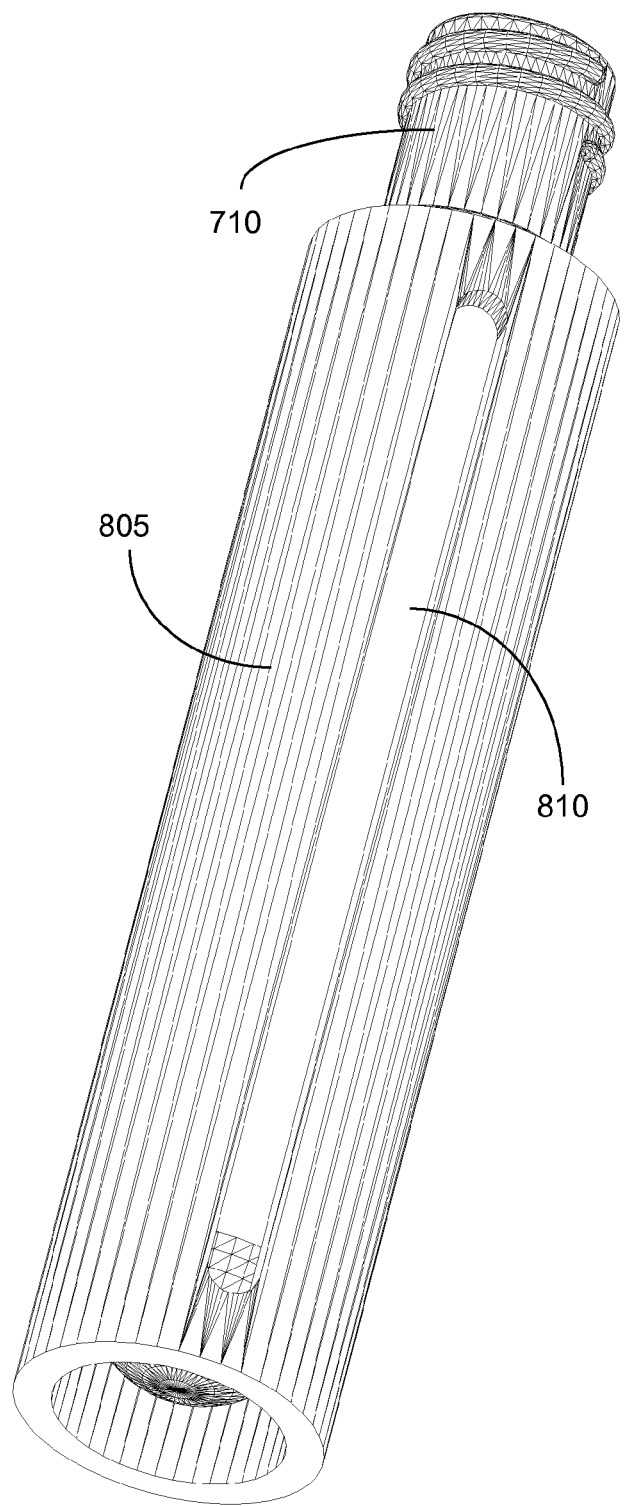
FIG. 8 shows a perspective view of a sample container and protective sleeve in accordance with an embodiment of the present invention.

FIG. 8 shows a perspective view 800 of a sample container 710 and a protective sleeve 805. The protective sleeve 805 has a slot 810 that permits viewing of the contents of the sample container 710 for embodiments of sample container 710 that are transparent. The protective sleeve 805 may be fabricated from cardboard or a polymer foam.

Figure 9:
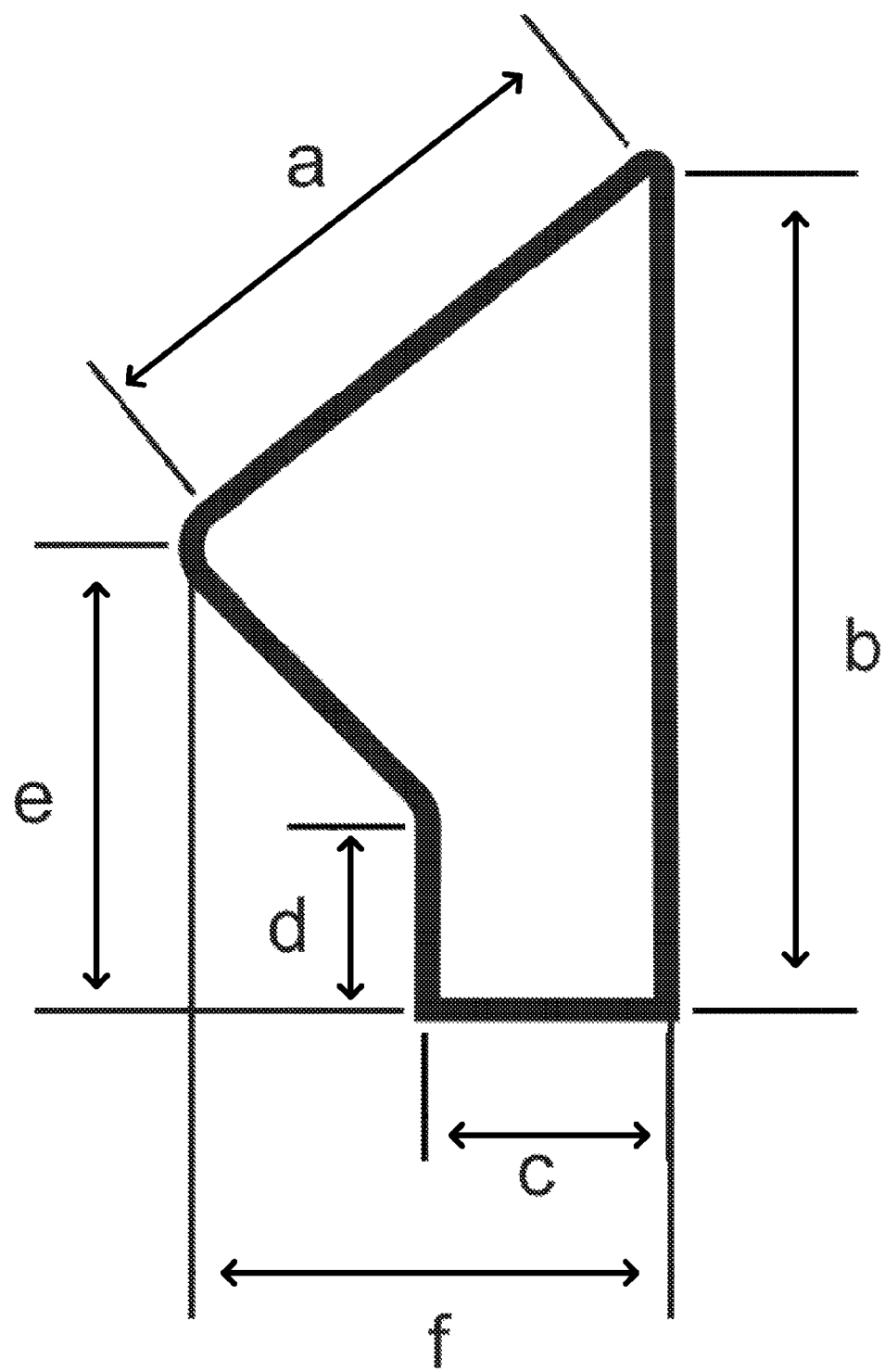
FIG. 9 shows a dimensional side view of the ergonomic adapter in accordance with an embodiment of the present invention.

FIG. 9 shows a dimensionally defined cross-sectional view 900 of an embodiment of an ergonomic funnel. The effective funnel opening width (a) is measured from the lowest point of the funnel rim to the highest point and is 25-80 mm with a preferred range of 30-50 mm. Dimension (a) may form the funnel midline as well as a vertical reflection plane when extended into a second vertical dimension through the radial center of the sample container. The overall height (b) of the ergonomic funnel is 35-100 mm with a preferred value of 50-70 mm. The lower opening diameter (c) is appropriately sized to the sample container of 10-30 mm with a preferred diameter of 12-18 mm. The neck height (d) is designed to fully cover the sample container attachment mechanism when fully assembled at 10-20 mm with a preferred value with 12-18 mm. The height of the sampling side (front) of the funnel (e) is shown and may be 10-80 mm with a preferred height of 28-40 mm. The ergonomic funnel minor axis (f) as measured at its widest point may be 20-60 mm with a preferred width of 25-35 mm.

Figure 10:
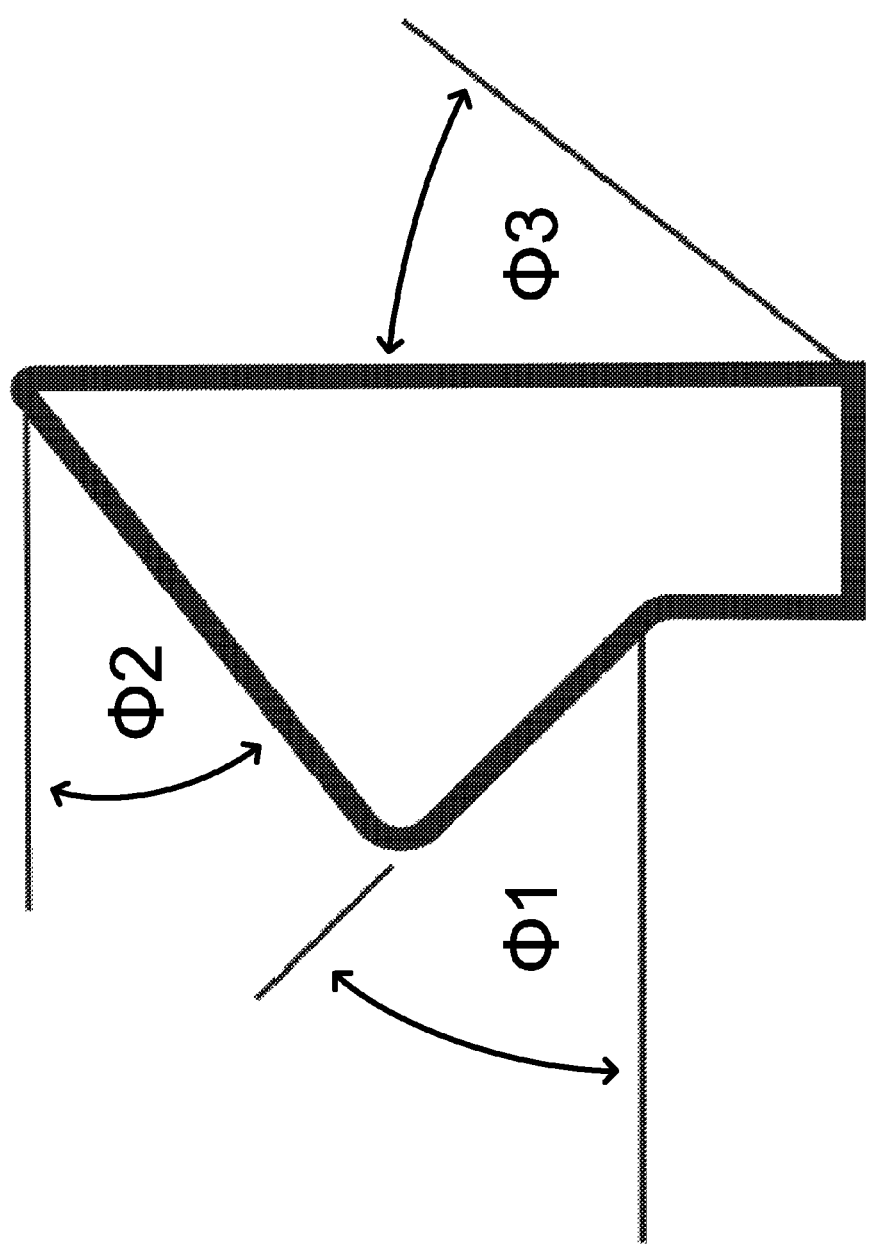
FIG. 10 shows a side view of the ergonomic adapter with angle definitions in accordance with an embodiment of the present invention.

FIG. 10 shows a side view 1000 of the ergonomic funnel of FIG. 9 with angle indications. The funnel opening angle $\Phi_1$ as defined by the angle of the plane of the funnel rim below horizontal may be 25-70 degrees with a preferred angle of 30-50 degrees. The funnel front slope angle $\Phi_2$ is defined as degrees above horizontal and may be 15-70 degrees with a preferred range of 35-55 degrees. The privacy angle $\Phi_3$ as defined by degrees from vertical may be −(minus)20 to +20 degrees with a preferred embodiment including the range −(minus)5 to +5 degrees.

Figure 11:
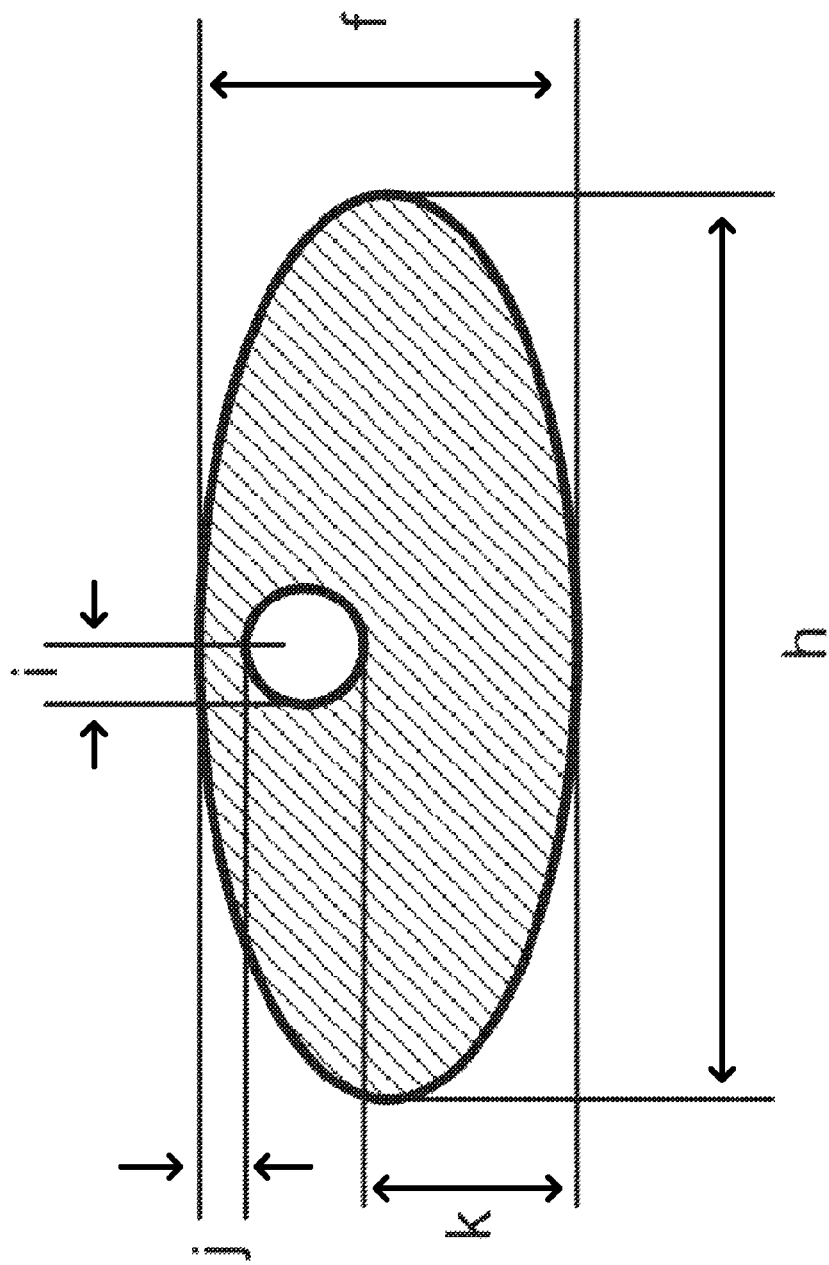
FIG. 11 shows a top view of the ergonomic adapter with dimensions indicated in accordance with an embodiment of the present invention.

FIG. 11 shows a top view 1100 of the ergonomic funnel of FIG. 9 with dimensional indicators. Funnel minor axis (f) is defined above in FIG. 9. Ergonomic funnel major axis (h) is taken as the widest measurement of the funnel rim opening and may be 40-120 mm with a preferred width being 50-90 mm. The inner radius of the lower funnel opening (i) that conveys the sample into the sample container ranges from 2-10 mm with a preferred value of 3-7 mm. For clarity, (i) is the radius of a circular embodiment of the described opening from which a diameter may be calculated. The lower funnel opening is located relative to the upper funnel rim as defined by the horizontal distance to the privacy edge (j) and may be 1-15 mm with a preferred range of 2-6 mm. The lower funnel opening is located relative to the upper funnel rim as defined by the horizontal distance to the sampling edge (k) and may be 8-30 mm with a preferred range of 12-20 mm. There are no implied restrictions that j<k other than those implicit within the dimensional embodiments.

Figure 12:
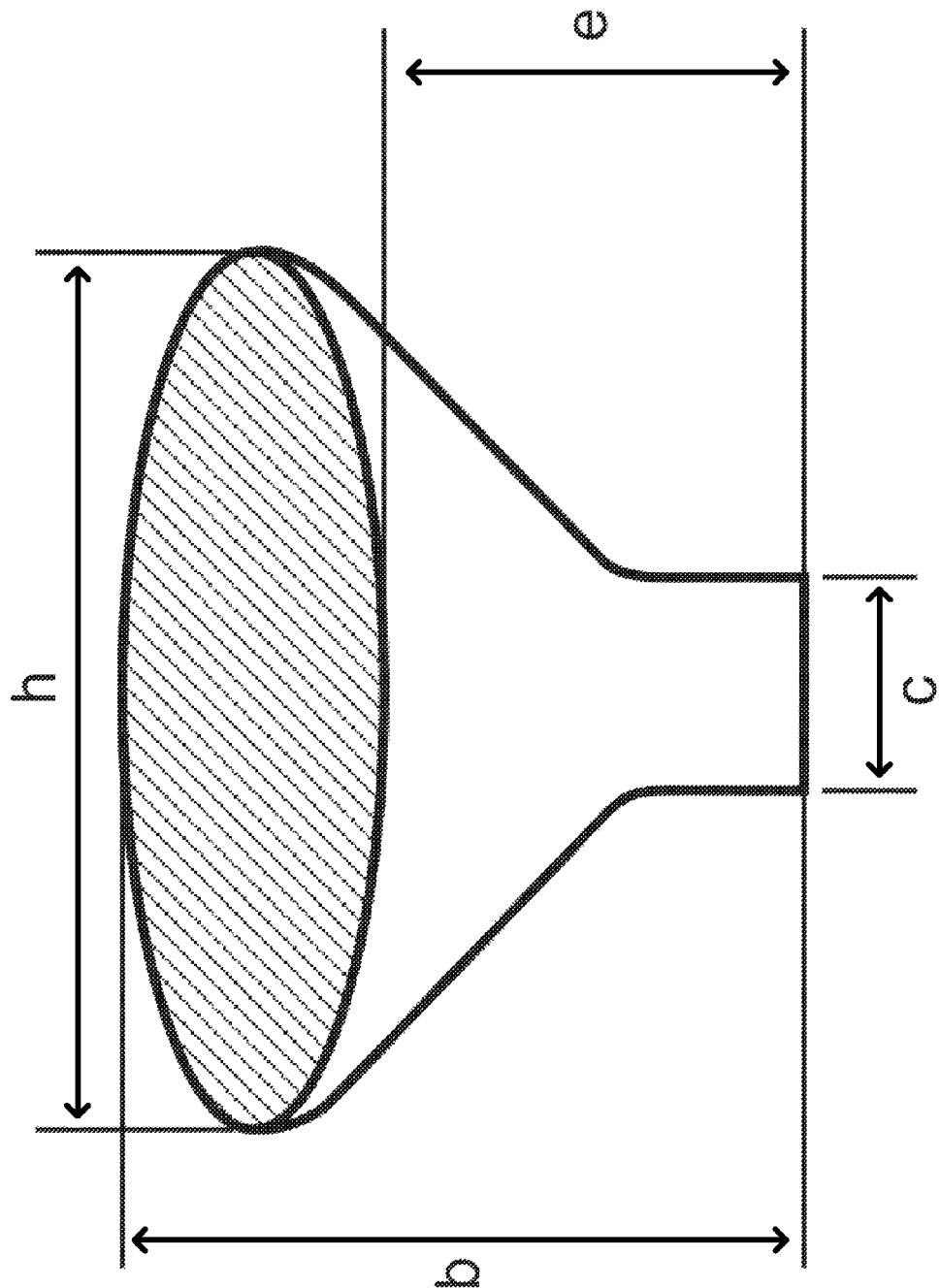
FIG. 12 shows a front view of the ergonomic adapter with dimensions indicated in accordance with an embodiment of the present invention.

FIG. 12 shows the front view 1200 of the ergonomic funnel (interior surface shaded) of FIG. 9. The funnel major axis (h), overall height (b), lower opening diameter (c) and sampling rim height (e) are as described and defined in previous figures.

Figure 13:
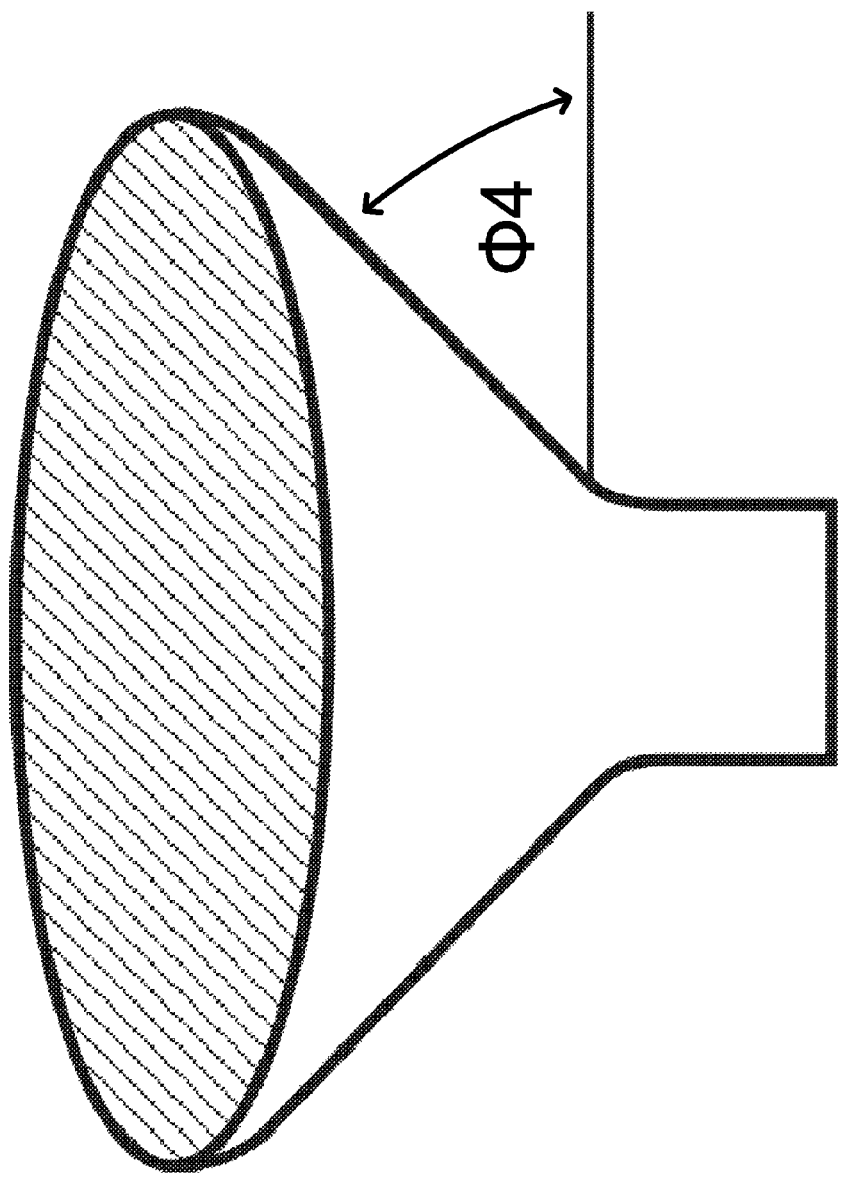
FIG. 13 shows a front view of the ergonomic adapter with additional angle definition in accordance with an embodiment of the present invention.

FIG. 13 shows a front view 1300 of the ergonomic funnel of FIG. 9 with funnel side angle $\Phi_4$ indicated as measured from horizontal which may range from 20-70 degrees with a preferred range of 40-55 degrees.

Figure 14A:
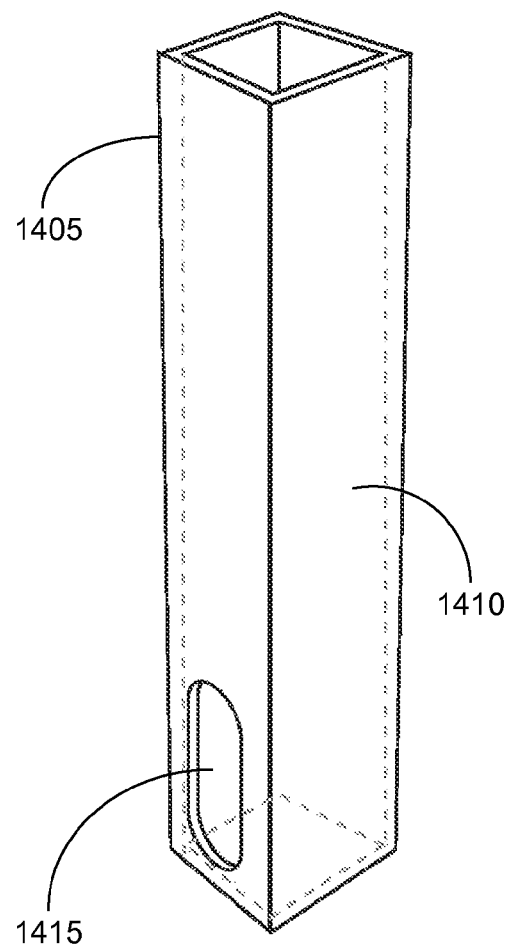
FIG. 14A shows a perspective view of a sample collection tube sheath in accordance with an embodiment of the present invention.

FIG. 14A shows a perspective view 1400 of an embodiment of a sample container sleeve 1405 that provides a labeling surface 1410 and a sight window 1415. The container sleeve reduces the amount of ambient light that reaches the sample potentially degrading sample as well as reducing visual access for personnel to the provided sample. The container sleeve 1405 also provides structural support and protection for the interior container that may be fabricated from a breakable material such as glass. The sight window 1405 allows the volume of sample to be judged to be adequate based on the manufactured height of the window the volume range can be tightly controlled. The sample container sleeve 1405 may be fabricated from cardboard. The sleeve bottom may be open or closed with closed being a preferred embodiment, providing accurate indication of sample height. An open bottom sleeve is equally preferred provided that a mechanism exists to ensure that the sleeve is accurately positioned on the sample container such as adhesives or guidance markings.

Figure 14B:
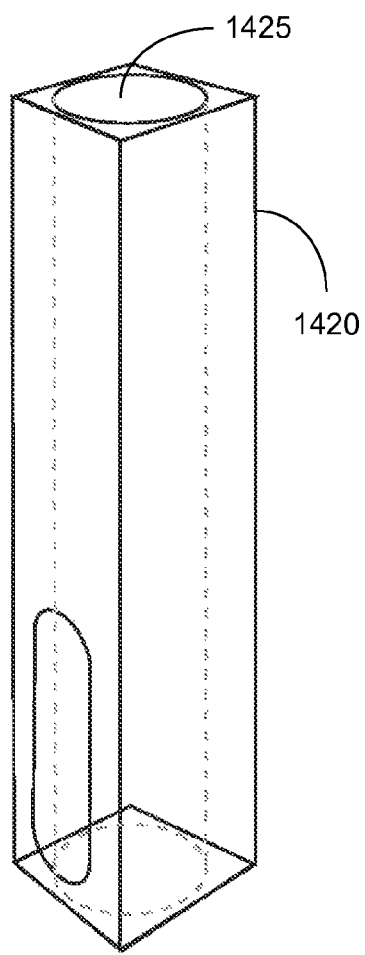
FIG. 14B shows a perspective view of a sample collection tube sheath with a round bore in accordance with an embodiment of the present invention.

FIG. 14B shows a perspective view 1401 of an embodiment of a sample container sleeve 1420 that is similar to the sample container sleeve 1405 of FIG. 14A; however, the bore 1425 of sample container sleeve 1405 is round in order to better conform to a round sample container. The sample container sleeve 1420 may be fabricated from a polymer foam (e.g., Styrofoam). The sleeve bottom may be open or closed with closed being a preferred embodiment, providing accurate indication of sample height. An open bottom sleeve is equally preferred provided that a mechanism exists to ensure that the sleeve is accurately positioned on the sample container such as adhesives or guidance markings.

Figure 15:
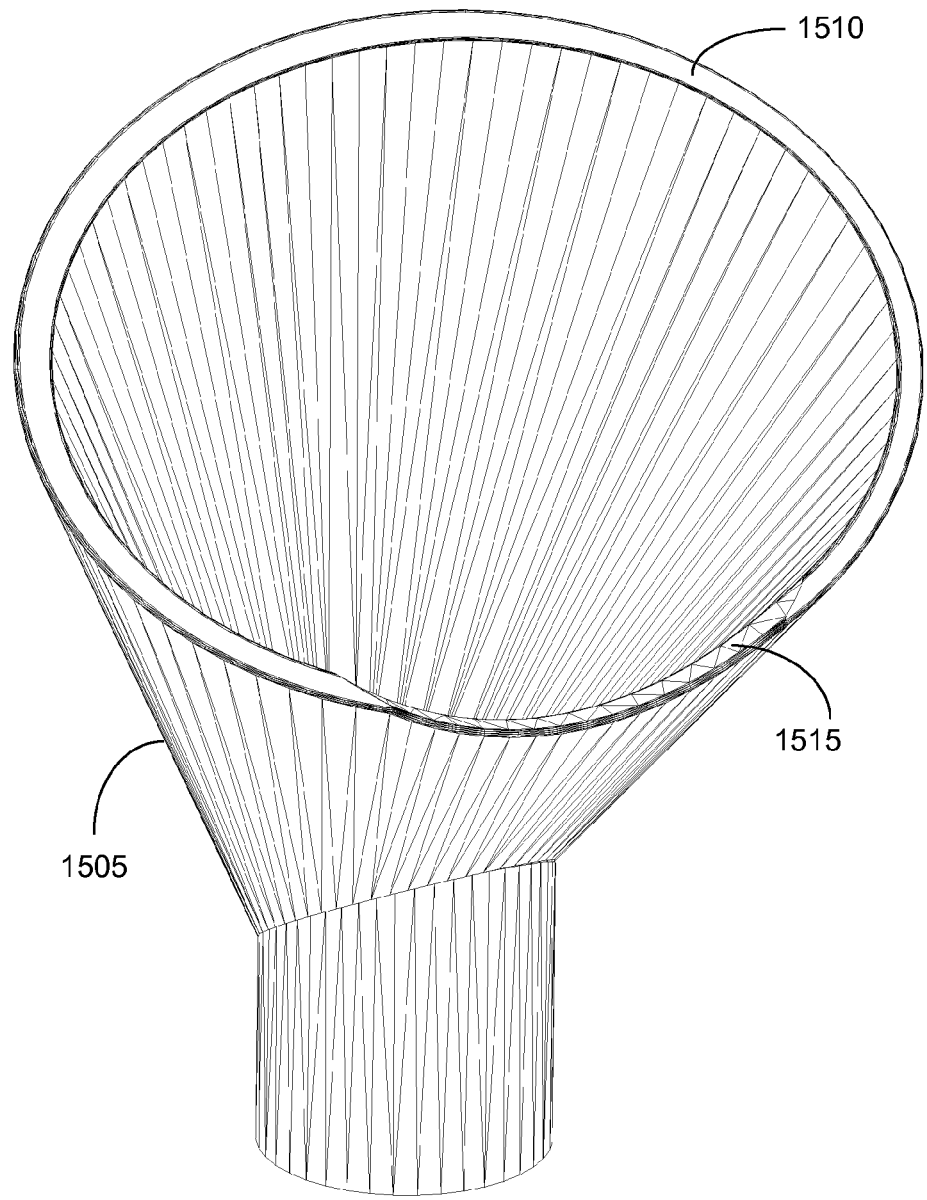
FIG. 15 shows a perspective view of a sample collection adapter in accordance with an embodiment of the present invention.

FIG. 15 shows a perspective view 1500 of an embodiment of a sample collection adapter 1505 having an upper planar rim 1510 with a curved cutout 1515 that serves as a contact surface for the lip of a subject providing an oral fluid sample. The sample collection adapter 1505 has a three-dimensional rim that is curved in two different non-parallel planes.

While the invention has been described in detail with reference to preferred embodiments thereof, it will be apparent to one skilled in the art that various changes can be made, and equivalents employed, without departing from the scope of the invention. For example, the conical funnel 105 shown in FIG. 1A and the ergonomic funnel 405 shown in FIG. 4A may be interchangeable with any of the depicted sample containers.

What is claimed:

1. An oral sample collection system comprising:
An ergonomic oral fluid sample funnel for receiving sample, wherein said ergonomic funnel is characterized by:
an effective funnel opening width of between 25 and 80 millimeters, a minor axis of between 20 and 60 millimeters, a major axis of between 40 and 120 millimeters, wherein said minor axis is less than said major axis and bounded by a sampling edge adapted to be contacted by a user's lip and a privacy edge located opposite of said sampling edge, configured to provide privacy when the user expectorates into said funnel, a sampling rim height of between 10 and 80 millimeters associated with said sampling edge, an overall height of between 35 and 100 millimeters associated with said privacy edge, wherein said sampling rim height is less than said overall height and is the minimum height of the funnel rim, a funnel front slope angle of between 15 degrees and 70 degrees, and a funnel opening angle and a privacy angle wherein said funnel opening angle is not equal to said privacy angle;
A threaded sample collection container adapted to be connected to, and disconnected from, threads located on said ergonomic sample funnel; and
A threaded sample collection container cap adapted to be connected to and disconnected from said sample collection container.

2. The sample collection system of claim 1 further comprising a closure liner for providing a seal at an opening of said sample container.

3. The sample collection system of claim 2 wherein said closure liner and said sample collection container are sorption neutral.

4. The sample collection system of claim 3 further comprising a compression disk for backing up said closure liner.

5. The sample collection system of claim 4 wherein said sample collection container cap comprises a hole for enabling sample extraction.

6. The sample collection system of claim 1 further comprising a label, said label comprising a minimum fill marking and a maximum fill marking.

7. The sample collection system of claim 1 further comprising a sheath for substantially surrounding and protecting said sample collection container.

8. The sample collection system of claim 7 further comprising a window in said sheath for permitting viewing the interior of said sample collection container.

9. The sample collection system of claim 1 wherein said ergonomic sample funnel comprises a thermoplastic polymer.

10. The sample collection system of claim 1 wherein said sample collection container comprises a glass.

11. An oral sample collection system comprising:
An ergonomic oral fluid sample funnel for receiving a said oral fluid sample, wherein said oral fluid ergonomic funnel is characterized by: an effective funnel opening width of between 30 and 50 millimeters, a minor axis of between 25 and 35 millimeters, a major axis of between 50 and 90 millimeters, a funnel front slope angle of between 35 degrees and 55 degrees, an upper planar rim with a single curved cutout adapted for contacting a user's lip located opposite of a privacy edge of said upper planar rim, said privacy edge is configured to block a view of the user providing said oral sample;
A threaded sample collection container adapted to be connected to, and disconnected from, threads located on said oral fluid ergonomic sample funnel; and
A threaded sample collection container cap adapted to be connected to and disconnected from said sample collection container.

12. The sample collection system of claim 11 further comprising a closure liner for providing a seal at an opening of said sample container.

13. The sample collection system of claim 12 wherein said closure liner and said sample collection container are sorption neutral.

14. The sample collection system of claim 13 further comprising a compression disk for backing up said closure liner.

15. The sample collection system of claim 14 wherein said sample collection container cap comprises a hole for enabling sample extraction.

16. The sample collection system of claim 11 further comprising a label, said label comprising a minimum fill marking and a maximum fill marking.

17. The sample collection system of claim 11 further comprising a sheath for substantially surrounding and protecting said sample collection container.

18. The sample collection system of claim 17 further comprising a window in said sheath for permitting viewing the interior of said sample collection container.

19. The sample collection system of claim 11 wherein said ergonomic sample funnel comprises a thermoplastic polymer.

20. The sample collection system of claim 11 wherein said sample collection container comprises a glass.

* * * * *